United States Patent [19]
Baker, Jr.

[11] Patent Number: 5,809,826
[45] Date of Patent: Sep. 22, 1998

[54] INFERENTIAL CONDENSATION SENSOR

[76] Inventor: Hugh M. Baker, Jr., R.R. 1, Box 2155, Lubec, Me. 04652

[21] Appl. No.: 688,160

[22] Filed: Jul. 29, 1996

[51] Int. Cl.[6] .............................. G01N 5/02; G01N 25/56
[52] U.S. Cl. .................................. 73/75; 73/75; 73/29.01
[58] Field of Search .............................. 73/29.01, 335.01, 73/73, 75

[56] References Cited

U.S. PATENT DOCUMENTS

| | | |
|---|---|---|
| 2,106,593 | 1/1938 | Deniston et al. . |
| 2,461,310 | 2/1949 | Cilley . |
| 2,584,988 | 2/1952 | Dember . |
| 2,680,371 | 6/1954 | Donath . |
| 2,904,995 | 9/1959 | Obermaier . |
| 2,975,638 | 3/1961 | Morrison . |
| 3,071,746 | 1/1963 | Kohl . |
| 3,139,085 | 6/1964 | Custance et al. . |
| 3,173,610 | 3/1965 | Feibush et al. . |
| 3,280,618 | 10/1966 | Ballinger . |
| 3,396,574 | 8/1968 | Hanlein et al. . |
| 3,748,625 | 7/1973 | Bennewitz . |
| 4,166,217 | 8/1979 | Bunnenberg et al. ...................... 73/29 |
| 4,215,568 | 8/1980 | Garber et al. . |
| 4,378,168 | 3/1983 | Kuisma et al. . |
| 4,579,462 | 4/1986 | Rall et al. . |
| 4,626,774 | 12/1986 | Regtien . |
| 4,677,416 | 6/1987 | Nishimoto et al. . |
| 4,843,867 | 7/1989 | Cummings .............................. 73/29.03 |
| 4,948,263 | 8/1990 | Herrmann et al. . |
| 5,139,344 | 8/1992 | Mutter . |
| 5,482,371 | 1/1996 | Nishizawa et al. .................... 73/29.01 |

Primary Examiner—Max H. Noori
Attorney, Agent, or Firm—Spencer & Frank

[57] ABSTRACT

A condensation sensor according to the invention detects condensation at a level of concern on a surface of interest. It has a thermally passive test surface that emulates the condensation-forming characteristics of the surface of interest, and has thermal conductivity, thermal capacity, and surface heat density sufficiently high that a detectable quantity of condensation forms on the test surface no later than formation of condensation at the level of concern on the surface of interest; and a sensor at the test surface that provides a signal in response to the presence of a detectable quantity of condensation on the test surface. The sensor may comprise two electrodes separated by an effective gap, the presence of a droplet of condensation at the gap closing a circuit between the two electrodes, and may further comprise a gathering mechanism for bringing droplets condensing on the test surface to the effective gap. A method according to the invention includes (a) providing a test surface, (b) emulating the condensation-forming characteristics of the surface of interest with the test surface, (c) passively thermally focussing the test surface so that the thermal conductivity, thermal capacity, and surface heat density are sufficiently high that a detectable quantity of condensation forms on the test surface no later than formation of condensation at the level of concern on the surface of interest; and (d) detecting the presence of a detectable quantity of condensation on the test surface as a signal in a detection circuit.

31 Claims, 7 Drawing Sheets

INFERENTIAL CONDENSATION SENSOR

BACKGROUND OF THE INVENTION

1. Field of the Invention

The present invention relates to an inferential condensation sensor. More specifically, the invention relates to a device comprising a test surface that emulates the condensation characteristics of a surface of interest, and a method for sensing condensation at a level of concern on the surface of interest by monitoring condensation on such a test surface.

2. Background information

There is value in knowing when condensation forms on surfaces in a given area, or on a given surface. Condensation, also referred to here as "dew," occurs when ambient air or another gas comes in contact with a surface of interest whose temperature is at or below the "dew point" of that air or gas, thus depositing the water or other vapor as condensate on that surface.

The formation of dew on surfaces which are at or below the dew point of the ambient air causes problems in many applications. In electrical or electronic apparatus, even minute dew droplets can create unwanted or unintended paths for electric currents to flow. These dew droplets are often low enough in resistance to create unwanted and unintended paths for electrical currents which can cause circuit failure or cause the circuit involved to behave differently than intended.

Larger electrical equipment which involves larger voltage and current capacities are generally less susceptible to the higher resistance paths of minute dew formations, but they can be meaningfully impacted as the dew accumulates into larger pools of water whose resistance to current flow reduces as that pool grows in size.

In HVAC (Heating, Ventilating & Air Conditioning) systems, dew often forms as the initial movement of cooled air travels through metal duct work toward the outlets or diffusers of the system. If the air in the immediate area of that diffuser is warm and high in relative humidity—and even more specifically, if that warm, relatively moist air has migrated upstream from the diffuser into the ducts, dew will often form as the metal walls of the duct work and diffuser are suddenly cooled by that inrush of cold (refrigerated) air. As the cooled air emerges through the diffuser causing swirls and eddies of the warm moist air in its immediate area engage the diffuser's cool surface and the duct walls immediately adjacent to it, dew may form on those surfaces. This condition occurs commonly when there are long intervals between the movement of the cooled air through the system and warm humid air in the room to be cooled has migrated well upstream in the air handling duct work. The same situation can occur in other areas of the HVAC system such as in the heat exchanger compartment, the blower area, etc.

Dew will often accumulate over a number of such cycles causing the formation of pools of stagnant water. These become the breeding areas for microbial organisms including Legionella (Legionnaire's Disease), fungi and molds—all potentially harmful to occupants of the area cooled by that HVAC system.

A detector for dew formation is useful in applying preventive or corrective action such as heating or drying when needed, or cooling and de-humidifying in other applications, rather than applying such corrective means on a constant basis which would be wasteful or cause other undesirable effects. There have been extensive efforts over the last several decades to design dew detectors, and many are available commercially.

Some devices measure water vapor in air rather than dew point, providing a generally linear measure of changing humidity. Custance (U.S. Pat. No. 3,139,085) and Bennewitz (U.S. Pat. No. 3,748,625) measure the change in electrical resistance. Kohl (U.S. Pat. No. 3,071,746) measures decreased resistance as moisture is adsorbed on a surface. Such devices do not address the issue of whether dew is in fact forming on particular surfaces of interest.

Most condensation sensors measure the dew point according to its definition—the precise temperature at which dew or condensation will form from air or another gas. These involve creating and controlling temperature variations within the device. In particular, such sensors cool a test surface using a Peltier device or other cooling means, and detect the temperature at which dew will form. A temperature near this point at the surface of interest indicates that the dew point is being approached. This method provides a measure of the onset of condensation but does not reliably predict or indicate the formation of condensate on the surface of interest, much less when a detrimental amount of condensation has formed. Thus, a dew point detector when used as a condensation sensor is prone to false positives and false negatives.

The dew point is generally detected as a change in physical or electrical properties of a test surface having special properties as dew forms on it. The measured properties can include resistance across a controlled gap between two or more electrodes, changes in other electrical parameters between similarly configured electrodes, changes in wave propagation across a controlled gap on a test surface, changes in reflectivity on a polished test surface, and numerous other methods. Feibush (U.S. Pat. No. 3,173,610) uses a dew droplet formed at the dew point to close a circuit between two otherwise electrically insulated elements (electrodes).

A very small, well controlled effective gap would be particularly beneficial for detecting changes in electrical parameters (resistance, conductance, capacitance, impedance, etc.) occurring between electrodes as dew formation occurs. Prior art devices do not create such a gap effectively with inexpensive, well controlled techniques. Regtien (U.S. Pat. No. 4,626,774) uses what appears to be a thin film technique, such as a printed circuit, to create an interlaced comb which could control the effective gap and increase the linear length of that gap.

Kuisma (U.S. Pat. No. 4,378,168) suggests causing a wave to propagate across the surface of a piezoelectric material (quartz or ceramic) and detecting the attenuation of that wave when dew drops form on that surface. The test surface must operate in high temperatures, and is heated to be cleaned. As the cooling process also generates heat, some sensors, Feibush, for example, use heat sinks to exchange or dissipate the heat to the air.

Obermaier (U.S. Pat. No. 2,904,995) notes at col. 3, lines 23–32 that in prior techniques for detecting dew formation, the amount of moisture necessary to cause electrical leakage occurs long after the dew point has been reached. To avoid this problem, Obermeier measures the liberation of heat of condensation rather than the physical presence of condensate.

One of the disadvantages of such methods is that they generally require placing the detector on the surface of interest. The detectors may involve high voltage or complicated circuitry so that they can interfere with, or be interfered by, test surfaces on which they are placed within operating electrical/electronic circuits.

Previous efforts to identify dew formation on a surface of interest without altering its electrical or physical properties have largely failed. This is generally due to previously unrecognized problems e.g. with placing dew detectors on a surface of interest and configuring the test surfaces. The surfaces of interest on which unwanted dew formation can occur are often inaccessible and have greatly varying physical configurations. For example, in a single electrical/electronic device, the wiring, printed circuit boards, components, connectors, etc. have such greatly varying surface configurations on which detrimental dew droplets may form that no specific test surface for any of the known dew detection methods would accommodate this great diversity. Yet, there is a long-felt need for a way to detect if dew at a level of concern is forming on any of these surfaces of interest.

Many dew point detectors are designed to be extremely sensitive to the early stages of dew formation and are small and consequently, they are relatively complex, cumbersome, and expensive devices.

SUMMARY OF THE INVENTION

The invention presents a new approach to sensing condensation. It does not vary temperature to determine dew point, thus avoiding costly, complex, cooling and temperature measuring systems. It does not measure humidity, but instead provides an abrupt, binary signal constituting a real time determination about the surface of interest at the point where dew formation becomes of concern, allowing control measures to be applied most efficiently.

According to the invention, great improvements in simplicity, reliability, and sensitivity to the actual concerns about dew formation are achieved by using a test surface that is representative of and emulates a surface of interest. Rather than incorporating the test surface within a complex dew point measuring or control instrument, the test surface of the invention can be designed and placed so as to be analogous to the surface of interest.

An advantage of the invention is that it produces copious quantities of dew on the test surface without altering ambient dew forming conditions. Another advantageous feature of the invention is its use of a "gathering device" to collect dew and apply it to the effective gap so as to enhance the sensitivity of the device, so that the detection apparatus can be more simple, less costly and more reliable. A further advantage of the invention is that an effective gap may be produced inexpensively and with fine tolerances using conductor/insulator laminates with which the effective gap can be reduced to less than 0.001" if desired. This is an improvement over printed circuit technology with which it is difficult to obtain a gap less than 0.007".

This invention is contrary to the teachings of the prior art as to predicting the dew point in a test surface. Rather than determining the precise point at which dew would begin to form, the invention determines a slightly later point at which dew formation is sufficient to cause concern. By making this trade-off, the invention omits the requirement of cooling or heating a test surface without sacrificing sensitivity to the real problem. It avoids the need to measure the temperature of the surface of interest. It uses modifications and improvements in preexisting approaches which were not previously known or suggested because of the entirely different approach of the prior art.

By detecting the very beginning of dew formation on a test surface, rather than predicting in advance the point at which dew will form, this invention provides advantages that were not previously appreciated. For example, the least expensive and most reliable method of detecting dew formation on a test surface may be used—detecting current passing through dew droplets which bridge a gap between very closely spaced electrodes of a simple detection circuit. In a preferred embodiment, dew droplets as small as 0.002" are readily detected.

The actual sensing device according to the invention, exclusive of circuitry, may be a cylindrical shape as small as 0.75" diameter and 0.75" high or smaller, and can be put almost anywhere in an electronic device's enclosure. Placed in that enclosure, if it indicated dew formation on its emulating test surface, it is virtually certain that the component leads, the connectors, etc, in that enclosure are also experiencing similar dew formation. Accordingly, the inventive device does not directly detect dew on that component, it inferentially detects its presence in a highly reliable fashion.

According to the invention, a device for detecting condensation at a level of concern on a surface of interest in an ambient environment comprises:

a thermally passive test surface that emulates the condensation-forming characteristics of the surface of interest, so that when the test surface is located in the ambient environment, a detectable quantity of condensation forms on the test surface no later than condensation forms at the level of concern on the surface of interest; and a sensor that provides an output in response to the presence of a detectable quantity of condensation on the test surface.

The device may further comprise a heat sink, the test surface and heat sink together having a combination of thermal conductivity, thermal capacity, and surface heat density sufficiently high that a detectable quantity of condensation forms on the test surface no later than condensation forms at the level of concern on the surface of interest, and the test surface and heat sink, in combination, having a thermal conductivity no less than that of the surface of interest. The heat sink may be at least partially thermally insulated to increase the surface heat density of the test surface, and may comprise a thermally insulated extension of the test surface.

The sensor may comprise two electrodes, separated by a gap at the test surface, the presence of a droplet of condensation at the gap closing a circuit between the two electrodes. The effective gap is preferably between about 0.0005 and about 0.015 inches, most preferably between about 0.002 and about 0.005 inches. The sensor may further comprise a detection circuit comprising means for applying a voltage across the electrodes and producing a current when a condensate drop bridges the effective gap. One electrode can be connected to the test surface and the other electrode can be a wire wrapped around the test surface with first and second alternating sections, the first sections having insulation and the second sections being exposed, the thickness of the insulation of the first sections providing an effective gap between the exposed wire of the second sections and the test surface.

The device may be a spiralled coil of two laminate pieces, each piece comprising an electrically non-conductive layer and an electrically conductive layer, the test surface being an end of the coil, and the circumference of the coil being thermally insulated, with one electrode connected to the conductive layer of one laminate piece, and the other electrode connected to the conductive layer of the other laminate piece.

The invention further provides means for gathering condensate droplets at the effective gap, such as open windings or screens of non-water absorbing, non-wetting filamentous materials. The filamentous material can be selected from the group consisting of fiberglass, nylon, other plastic, and a material coated with a material selected from the group, or in wax or varnish. Magnet wire, enamel coated or otherwise, is a preferred embodiment.

A laminate, comprising an electrically non-conductive inner layer and an electrically conductive outer layer, may be placed on the test surface, the test surface and the conductive layer being two electrodes, such that a gap is formed between the test surface and the edge of the conductive layer of the laminate, the presence of a droplet of condensation at the gap closing a circuit between the two electrodes. The laminate non-conductive layer is preferably between about 0.002 and about 0.005 inches.

The output can be a signal that switches from off to on, such as a visible alarm, an audible alarm, or activation of an electrical relay.

The test surface may economically be formed of a metal rod with a diameter between about 0.125 and about 2 inches, and length from about half to about three times the diameter.

The sensor may comprise a basal surface having first and second exposed electrodes, and the test surface is adjacent to and spaced apart from the electrodes by a gap, such that the simultaneous presence of a first droplet of condensation between the test surface and the first electrode and of a second droplet of condensation between the test surface and the second electrode closes a circuit between the two electrodes and the test surface.

The device may include a light source directed at the test surface, a photo-sensitive detector, and a detection circuit comprising an automatic gain control circuit, an amplifying circuit, and a threshold detecting circuit, in which a current threshold is selected below which the sensor provides an output to indicate the presence of dew.

The test surface can be thermally connected with the surface of interest by physical contact, be thermally insulated from the surface of interest, or the test surface and surface of interest may be physically isolated but in the same ambient environment.

The invention further relates to a system comprising a plurality of devices according to claim 1, and a condensation control system comprising means for eliminating condensation activatable in response to a signal from one or more of the devices, such as a heater or dehumidifier.

The device of the invention includes:
(a) means for emulating the condensation-forming characteristics of the surface of interest,
(b) means for passively thermally focussing the emulating means so that a detectable quantity of condensation forms on the emulating means no later than formation of condensation at the level of concern on the surface of interest; and
(c) means for detecting the presence of a detectable quantity of condensation on the emulating means.

The invention further contemplates a condensation sensor comprising a test surface, a laminate applied thereto, and a detection circuit, the test surface being electrically connected to the detection circuit as a first electrode, the laminate comprising an electrically non-conductive inner layer having a thickness of about 0.001" to about 0.010" placed on the test surface, and the laminate further comprising an electrically conductive outer layer electrically connected to the detection circuit as a second electrode, such that the thickness at the edge of the inner layer of the laminate forms a gap between the test surface and the outer layer of the laminate, the presence of a droplet of condensation at the gap closing a circuit between the two electrodes, and permitting detection in the detection circuit.

A method according to the invention includes, without regard to order:
(a) providing a test surface in the ambient environment,
(b) emulating the condensation-forming characteristics of the surface of interest with the test surface,
(c) passively thermally focussing the test surface so that the thermal conductivity, thermal capacity, and surface heat density are sufficiently high that a detectable quantity of condensation forms on the test surface no later than formation of condensation at the level of concern on the surface of interest; and
(d) detecting the presence of a detectable quantity of condensation on the test surface as a signal in a detection circuit.

The method may further include activating a means for eliminating the detectable quantity of condensation in response to the signal.

Further features and advantages will become apparent from a consideration of the description and drawings.

BRIEF DESCRIPTION OF THE DRAWINGS

The invention may be understood by reading the following detailed description of preferred embodiments, in reference to the accompanying figures, in which like reference numerals refer to like elements throughout, and in which.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

The invention provides a passive device for sensing condensation at a level of concern on a surface of interest of an item, comprising a thermally passive test surface on which a detectable quantity of condensation forms before damaging quantities form on the surface of interest. The test surface emulates the condensate formation characteristics of the surfaces of interest; does not alter the condensate formation conditions prevailing about the surface of interest; and produces sufficient amounts of condensate on the test surface to permit reliable detection very early in the condensate formation process.

By employing a test surface having such characteristics, a condensation detection apparatus according to the invention may be placed in the most advantageous location without the need to have any parts of the apparatus physically in contact with the surface of interest. Also, apparatuses according to the invention can use methods for detecting condensation formation which are both inexpensive to manufacture and very reliable.

An emulating test surface according to the invention has the following characteristics:

1. It is thermally passive, i.e., its only source of heat is the ambient air in which it is placed, or conduction from the specific surface of interest on which it is mounted.
2. It has thermal conductivity equal to or greater than that of the materials of the items whose surfaces are the surfaces of interest.
3. It has sufficient thermal capacity to absorb enough latent heat of condensation to produce enough dew to be detected by the dew detecting apparatus by or before the time enough dew has formed on the surface of interest to be of concern to its user.
4. It is configured so as to facilitate the implementation of the dew detection method of choice using this emulating test surface as its test surface. For example, the test surface may be configured optimally for the placement of electrodes in a dew detector which detects changes in electrical parameters caused by dew formation, or for reflective surfaces whose surface reflectivity characteristics will be similarly changed, etc.
5. It is configured to optimize a characteristic which can be expressed as high "surface heat density" which may be defined as the amount of heat stored in a body which would be available at its thermally exposed surface to exchange (absorb or adsorb) heat via conduction or via convection at that thermally exposed surface. High surface heat density concentrates at the test surface a greater amount of heat absorbing capability to produce a greater quantity of dew than if that heat capacity were distributed over a greater surface area of the sink.

A high surface heat density can be achieved in several ways or combinations of ways. It is apparent that the physical shape of the sink having a given thermal capacity will greatly influence its surface heat density. The surface heat density of a rod whose length is approximately equal to its diameter is considerably higher than a body of the same material and mass whose form is a long slender rod (or wire). A cube of the same material and mass will have a higher surface heat density than that of the 1:1 diameter to length rod, and a sphere of the same material and mass would have an even greater surface heat density.

Thus in general the volume of the sink divided by its surface area is proportional to the surface heat density. Surface heat density goes up as the volume goes up and the surface area goes down.

Another very effective way to substantially increase the surface heat density for any given physical form is to reduce its thermally exposed surface by thermally insulating substantial portions of its otherwise exposed surface. For example, the surface heat density of a cube is increased by approximately five fold if all but one of its surfaces is thermally insulated. If that one thermally exposed surface is the test surface, it produces greater quantities of dew there than would be produced if the entire surface of the cube was exposed to the ambient air.

The detectors of the invention are typically constructed with a heat (or cold) sink to enhance dew formation by helping dissipate heat.

A test surface according to the invention is said to be thermally focussed if it satisfies all these conditions. That is, a test surface is thermally focussed if it is thermally passive and has thermal conductivity, thermal capacity, and surface heat density all sufficiently high that a detectable quantity of condensation forms on the test surface no later than formation of condensation at a level of concern on the surface of interest.

Empirical methods may be used to determine whether the end result of a thermally focussed heat surface is achieved. If not (that is if condensation forms to a level of concern at the surface of interest prior to formation of a detectable quantity of condensation at the test surface) then simple manipulation of the parameters described here allow a thermally focussed surface to be achieved. Thus, a person of ordinary skill may employ the methods and components described here to provide a test surface that is thermally focussed and emulates the characteristics of any given surface of interest.

The term dew is used here interchangeably with condensation. It should be understood that the devices and methods of the invention are applicable to condensation of any liquid from vapor in any gas, at any temperature range, although the application with condensation of liquid water from water vapor in air in the temperature range between the freezing and boiling points of water is the most common.

When the dew detection method is one which is predicated on changes in electrical parameters, particularly those using a change in electrical resistance (conductivity) between two electrodes, a farther enhancement of the test surface emulation may be achieved by employing a gathering mechanism which will tend to bring dew which has formed over the test surface to the effective gap. This gathering mechanism is one which takes advantage of water's natural tendencies to coalesce (when small independent droplets are caused to come in contact with one another and form larger drops), and to wick or migrate along narrow passages. Properly implemented, these gathering mechanisms can cause the gathering and migration of minute quantities of dew formations so as to bring greater quantities of dew to the effective gap or other most sensitive portions of the emulator's test surface thus both enhancing the reliability of the detection of the forming dew and causing the detection of the dew at an earlier stage of its formation.

Dew gathering mechanisms may be in the form of open windings, screens or irregular mesh made from non-water absorbing, non-wetting materials such as fiberglass, nylon and other plastics or of other materials which have been coated in wax, varnish or similar finishes. The test surface may also be modified by treatments that encourage "beading" of condensate droplets. For an effective gap type of sensor, the surface treatment must be electrically conductive.

The invention also provides an improved simple, inexpensive, approach to producing an accurate effective gap between electrodes for detecting the presence of dew drops. For example, the electrical insulating layer of a polyester-copper laminate can be used to produce an effective gap of less then 0.001" if desired.

Thus, the invention provides a new generation of inferential condensation sensor that can detect when water vapor is likely to be condensing on electronic/electrical components and circuits, on walls of HVAC air handling systems, and so on. A sensor device according to the invention indicates the presence of dew or water vapor condensation on surfaces in its immediate vicinity. The sensor is capable of indicating the presence of condensed water vapor droplets as little as 0.002 inch in height. Under certain conditions, it can indicate the imminent formation of condensed water vapor just before surfaces or components of interest actually experience the formation of condensed water at a level of concern. The sensor is not a quantitative sensor—it is essentially binary. Condensed water vapor is indicated as present, or it is not. The sensor is not prone to false alarms, and is not sensitive to humidity (water vapor). The sensor does not alter the conditions which determine the potential for condensing water vapor on the surfaces of interest, and is essentially passive in its normal state. The sensor may be configured to be sensitive to water vapor condensing conditions on surfaces in an area of concern, or on a specific surface area.

Figure 1:
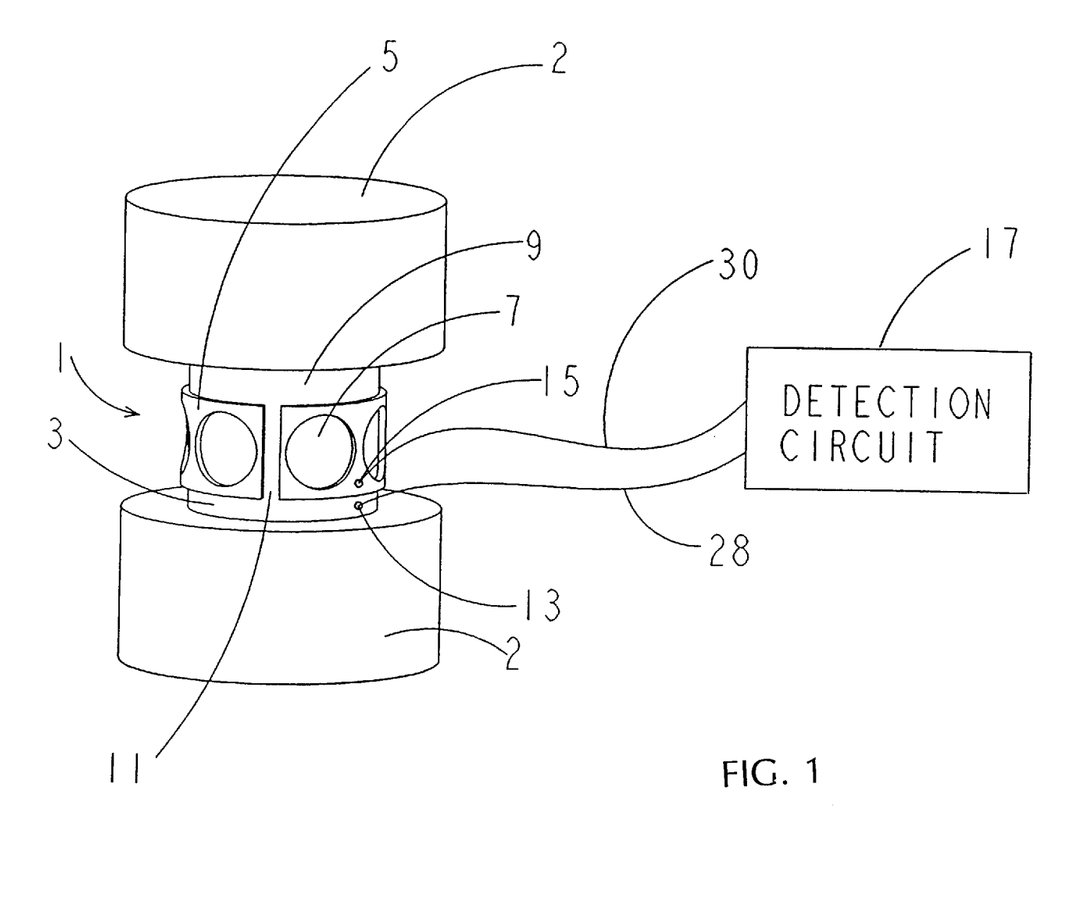
FIG. 1 illustrates a device according to the invention, including a test surface electrically connected to a detection circuit. The test surface is vapor-impermeable and is part of a detector assembly comprising an integral heat sink which is thermally insulated (as shown) or not insulated (not shown).

In the embodiment shown in FIG. 1, thermally conductive rod 1 made of copper or gold, or other material having high thermal conductivity and capacity, is in a configuration wherein its length is roughly three times its diameter. Both ends of rod 1 and approximately ⅓ of its length from both ends and the ends as well are covered with thermal insulating material 2. This increases the surface heat density by a factor of approximately three over the inherent surface heat density of a fully exposed rod of those proportions. Test surface 3 in this embodiment is the exposed circumferential band between the edges of the thermal insulating material. These elements configured as described form an emulation of surfaces of interest such as circuit boards, wires, connectors, cables, HVAC passageways, and so on.

Figure 2:
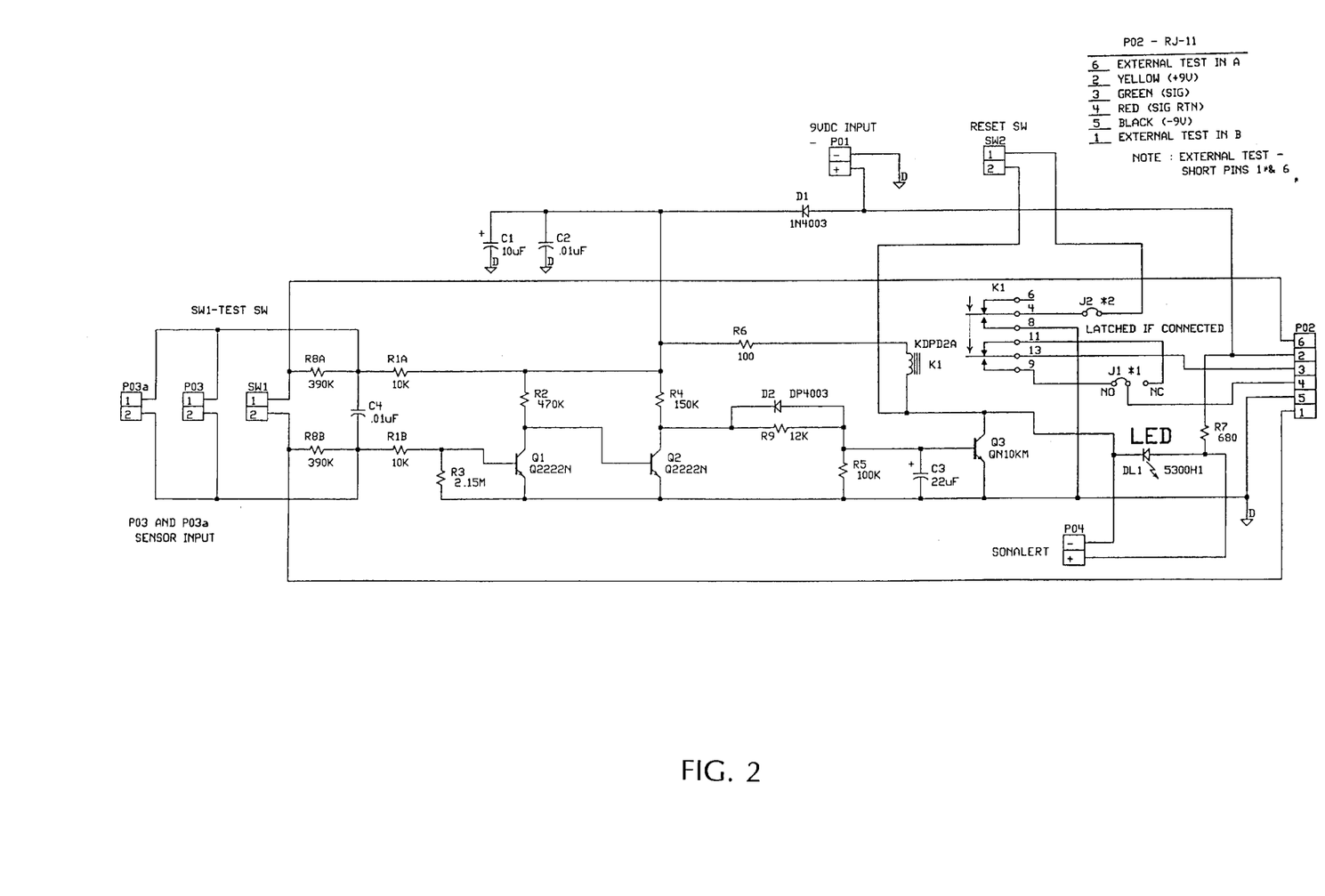
FIG. 2 shows a detection circuit for use with a test surface according to the invention.

The dew formation detection method selected for a preferred embodiment is one in which a change in the electrical resistance (conductivity) is caused by dew formation which physically and electrically bridges the gap between two closely spaced electrodes 13 and 15 of an electronic circuit such as shown in FIG. 2. This gap between electrodes may be referred to as the "effective gap". Many variations on this circuit will be apparent to those skilled in the art. Also, dew formation detection methods involving other electrical and physical parameter changes caused by dew formation may be applied to the test surface (3) of FIG. 1 with equal ease.

The smaller the effective gap between the two electrodes of the circuit shown in FIG. 2, the earlier in the dew formation process its existence can be detected. Similarly the greater the linear length of that physical gap, the more reliable will be the detection and in all probability, added length of the effective gap will cause the detection to occur at an earlier stage of the dew formation on the test surface. It is desirable to achieve these desired parameters of the gap between the electrodes with the use of manufacturing methods and materials that are not exotic or expensive.

To achieve these objectives, strip 5 preferably of polyester/copper laminate may be prepared as follows. The laminate may have nominal 0.001" thick layer of copper on electrically insulating material with thickness between about 0.002 to 0.005" which establishes the "effective gap". The width of strip 5 may be the width of test surface 3 less a nominal 0.040" so as to leave a space 9 approx. 0.020" wide between it and the top and bottom of thermally insulating caps 2 when wrapped around the exposed test surface 3 of rod 1. The length of strip 5 may be the circumference of test surface 3 less nominally about 0.02 to about 0.03" (20–30 mil) to leave a space 11 between the ends of laminate 5 when tightly wrapped around rod 1.

Strip 5 may be cut as a rectangle with round holes 7 punched in it to increase the length of the effective gap. The diameter of holes 7 may be nominally 80% of the width of strip 5. A desirable number of holes is that which will fit within the length while leaving approx. 0.030" between the circumferences and any other edge. The laminate thus has three types of spaces—between the ends of the wrapped strip of laminate 5 where those ends nearly meet at 11, between the laminate strip's top and bottom edge and the respective edges of the thermal insulating material, visible at 9, and the total of the circumferences of the punched holes 7.

Formed laminated strip 5 is wrapped as a band around the test surface of the rod as shown in FIG. 1 with the copper layer to the outside and the polyester layer between that copper layer of the laminated strip and the test surface of the rod.

The outer copper layer of laminate strip 5 is electrically connected at junction 15 via a wire to an outer electrode connection in detection circuit 17, shown in detail in FIG. 2. Copper rod 1 is connected at junction 13 via a wire to detection circuit 17 to become the other electrode (the inner electrode) of detection circuit 17. The polyester layer of laminate 5 maintains electrical isolation between inner electrode (the exposed surface 3 of rod 1) and the outer electrode (the copper outer layer of laminate strip 5). The electrodes are interchangeable. The thickness of laminate strip 5 establishes the effective gap between these two electrodes. Polyester/copper laminates are readily available with a wide range of thickness down to 0.001 inch for either layer. For most applications, it is felt that the optimum effective gap for the dew detection method which detects changes in resistance between the closely spaced electrodes is between about 0.002 and about 0.005 inch. The effective gap is thus uniform throughout the entire length of all edges of the laminate, although it could vary according to the invention.

As stated above, increased linear length of the effective gap enhances the reliability of detection of dew formation and tends to allow that detection at an earlier stage of dew formation. In the embodiment described herein, the linear length of the effective gap is the total length of the four edges of the laminate plus the total length of the circumferences of the circles (or other forms) cut in the laminate strip. Any dew formation along any portion of that length which grows to the height of the chosen effective gap between the electrodes will electrically bridge that gap and activate the circuit shown in FIG. 2 to indicate the presence of the dew formation.

For the vast majority of applications where fast response is desired many materials would have suitable thermal and electrical conductivity to serve as a test surface. Gold, silver, platinum, copper and aluminum are all excellent for their thermal capacity and thermal conductivity. Electrical conductivity is far less critical since it is easily compensated for in the companion detection circuitry. A preferred material is copper with a gold flash on the exposed surfaces to control copper's tendency to oxidize. Copper has appropriate thermal (and electrical) properties and is cost effective. Aluminum has desirable thermal properties and is cost effective, but if its surface is to be one of the electrodes, it can be difficult and somewhat expensive to keep that surface electrically conductive by plating it.

As to thermal insulation, styrofoam has excellent thermal insulating properties but is not very durable unless protected. Polystyrene is a hard, castable, machinable, inexpensive plastic material with very good thermal insulating properties. It can be used for both the basic structure of the device as well as for the thermal insulator covering much of the copper rod to increase its surface heat density. There are on the market many "vinyl based foams" which are available as a thick liquid (in a solvent). They are used to coat the handles of pliers and other tools to give them a softer feel and provide electrical insulating properties. Like most vinyls, these materials are good thermal insulators, are not expensive, and can be poured or brushed on. Similar coatings are made from solvent based rubber and acrylic latex compounds which have excellent thermal insulating properties when the solvent evaporates. Rubber and wood would be satisfactory from a thermal standpoint.

The dimensions of the rod and many other design parameters are primarily determined by manufacturing convenience. Rod diameter may desirably be between about 0.125" and about 0.500", for example 0.375." Rod length may be about the same as or up to roughly 2–3 times its diameter, for example 1.7 times the rod's diameter. The test surface, including that portion which is covered by the outer electrode and the gathering mechanism is about 1% to about 99% of the total surface area, preferably about one quarter to three quarters of the total surface area, most preferably about 40–50% of the rod's circumferential surface. In a preferred embodiment, the remainder of the rod's circumference and its two ends are covered by thermally insulating polystyrene plastic material, so that roughly two thirds of the rod's total surface is covered. Of the one third which is uninsulated, roughly 30% is covered by the laminate and another 10–15% is covered by filamentous material, e.g. magnet wire wrapping. The remainder, about half of the uninsulated surface, or about 15% of the rod's total surface area, is fully exposed to the ambient air. Variations in any of these ranges of ±10% or greater, depending on the material and configuration, would have no meaningful impact.

The thickness of the non-conducting laminate layer providing the effective gap may be in the range of about 0.001 and about 0.005 inches in normal applications with 0.002 to 0.003 inches preferred. Laminated material is commercially available in a wide range of both copper and electrical insulating layer thicknesses. Laminate material preferably does not absorb water or water vapor such that its electrical conductivity increases.

An effective gap of less than 0.001" may provide spurious nuisance readings. However, that nuisance may be justifiable in certain applications for the somewhat earlier detection that may result. Normally, the upper limit of the size of the effective gap is determined by the size of the dew droplet that would need to form to bridge the gap. In some applications one would want the dew detection delayed until water accumulations reach 0.010 to 0.015 inches. For the majority of applications the range of 0.001 to 0.005 inches is optimal, for example 0.003".

The circuit shown in FIG. 2 is a representative example of a detection circuit. Other circuits known in the art could be used instead if they provide the necessary signal at the point where condensation bridges the gap between the inner and outer electrodes. In general, the circuit applies a voltage between electrodes which are normally an open circuit with infinitely high resistance, and detects the change in resistance which typically falls to somewhere between about 100K and about 500K ohms when a drop of water (dew) bridges them. This is a binary result, i.e., the water bridges the electrodes or it does not. Because the current that passes through a dew drop is too small to light a bulb or activate a relay, the circuit amplifies that current enough to power the indication of the dew's presence.

Through resistors RIA and RIB, 9 VDC from connector pins 2 and 5 of connector P02 is applied to the sensing electrode input leads connected at P03 and/or P03a pin 1 to the inner electrode 13 and at P03 and/or P03a pin 2 to the outer electrode 15 at test surface 3. Normally, there is no current across the effective gap which electrically separates the inner and outer electrodes. Any dew formation bridging that effective gap will pass a small amount of current which is then amplified through Q1, Q2 and Q3. In this circuit, the amplified current from Q3 drives the LED indicator DL1, an optional audible signalling device (sonalert in this example) via connector P04, and the coil of relay K1 causing it to energize and transfer its contacts. K1 serves to electrically isolate this circuit's output from any electrical voltages the sensor assembly may come into contact with. Its isolated ON/OFF output (switch) is expressed through pins 3 and 4 of connector P02. Means are provided to change the configuration of K1's contacts at pins 3 and 4 of P02 to be normally open or normally closed by exchanging the position of the movable jumper J1. The transfer of K1's contacts can be configured to be either on a real time basis, i.e., the contacts activate when dew bridges the effective gap and de-activate when that dew drop disappears, or by placing a jumper connection at J2, K1's contacts will remain activated, in a "hold" mode, even after the dew droplet has disappeared. The held contacts are released to the currently normal position by activating the "RESET SWITCH" SW2 thus opening its normally closed contacts.

Some delay (nominally 0.25 sec.) in the de-activation of the output devices is caused as a result of diode D2, resistor R5 and capacitor C3. This delay avoids the "chatter" which might otherwise occur as a dew drop just barely bridges the effective gap either as it forms initially or as it subsequently disappears. A simple "CIRCUIT TEST" capability is provided through resistors R8A and R8B by making a short circuit connection between pins 1 and 6 of P02 or by closing switch SW1 which is normally open. This effectively connects R8A and R8B which will bridge the electrode connections (P03a or P03b) with 780K ohms to simulate the resistance change caused by a dew droplet bridging the effective gap.

The circuit applies a voltage (preferably less than 30 volts) across the electrodes and amplifies the current that voltage will push through a dew drop (whose resistance would typically be 500,000 ohms or less) sufficiently to activate an output device—an LED, a relay, or the like. In the simplest case, an ordinary ohmmeter can give an indication of dew's presence.

While a copper/polyester laminate is discussed in connection with the embodiment of FIG. 1 and the other illustrated embodiments, other laminates having an electrically conductive material as one layer and an electrically insulating material as the other layer will be equally satisfactory. The thermal properties of the laminate materials are not very important since the outer electrode typically covers a relatively small portion of the test surface so as to diminish interference with this surface's ability to exchange heat between the ambient air and the mass of the heat sink which is the copper rod. Dew will form over the inner and outer electrode's surfaces, but with its far greater thermal capacity, much greater quantities of dew will form on the exposed surfaces of the inner electrode (the rod). Since dew formation occurs over all of the surface of the inner electrode left uncovered by the outer electrode, the vast majority of that dew will form in areas which are not immediately adjacent to the effective gap.

Figure 3:
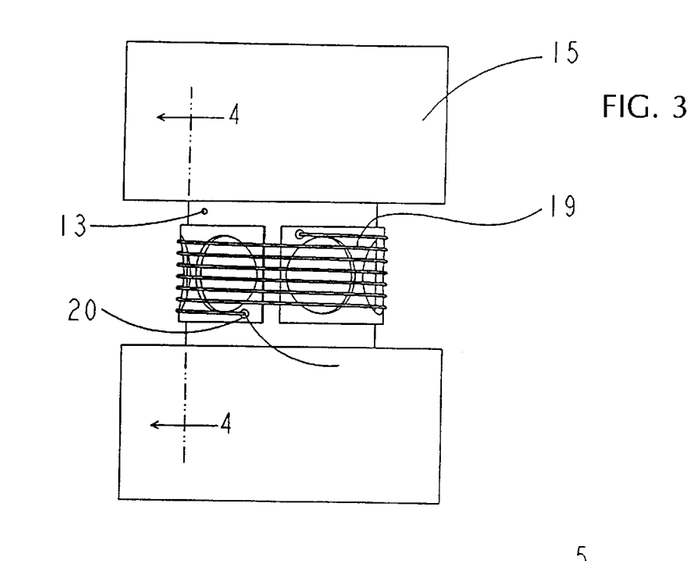
FIG. 3 shows a test surface wound with filaments to gather condensate.

To bring greater quantities of dew forming on the test surface to the effective gap where it can be sensed, strands of non-wetting and non-moisture absorbing material such as nylon, polyester, enamel coated wire, etc. are wrapped circumferentially around the outer electrode band as shown in FIG. 3. Strands 19 of filamentous material are wrapped around the outside of strip 5 repeatedly, preferably in windings. The material may be any material of suitable strength that is electrically non-conductive, does not absorb water or the condensate of interest, and may be magnet wire (AWG #30 for example) or nylon monofilament with a diameter nominally about 8 mil, or nylon, polyester, other plastic, or wire coated with wax, enamel, polyurethane, or any other suitable available material. In this embodiment, the magnet wire wrapping starts at one corner of the outer electrode 15 and ends on or near the opposite corner of the outer electrode's other end. The magnet wire may serve to hold the laminate in place.

In one embodiment, shown in FIG. 3, 30 gauge enamel coated magnet wire is used. The starting point is soldered at starting joint 20 on the outer electrode, and after a sufficient length is wound around laminate strip 5, a solder joint is made to physically join the wire to the copper outer surface of strip 5 and also establish an electrical junction 15. The free end of strand 19 is continued and then connected to detection circuit 17 as the outer electrode. Five wraps may be sufficient. Another piece of the magnet wire or other wire is soldered to the copper rod's exposed surface 3 to be connected to the inner electrode lead of circuit 17. As magnet wire has a thin coating of insulating varnish or enamel, it does not short the inner to the outer electrode. Upon soldering, the insulation is removed to make electrical contact.

Figure 4:
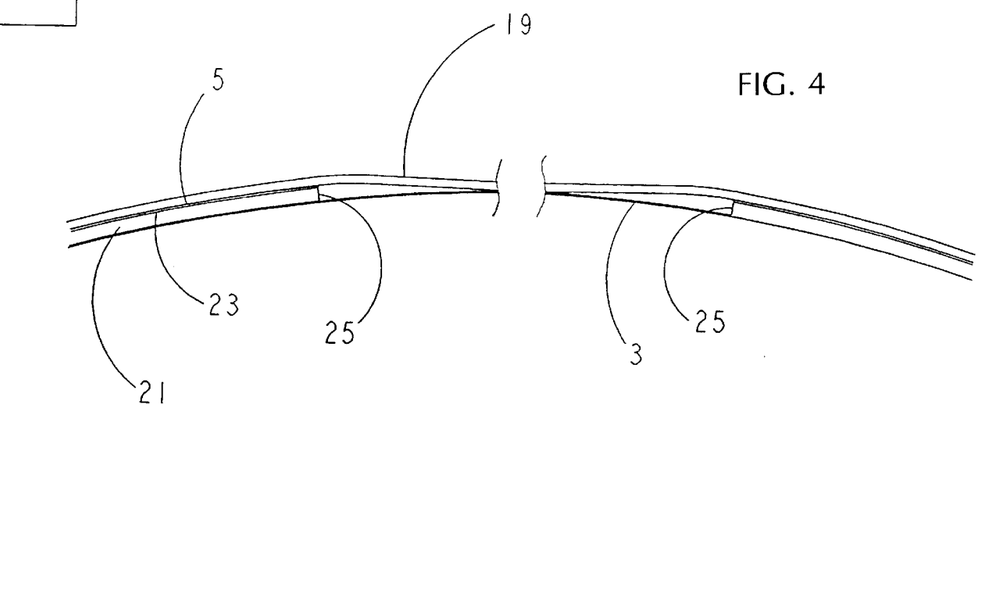
FIG. 4 is a sectional view taken along the line 4—4 of FIG. 3, showing windings against the effective gap between inner and outer electrodes.

FIG. 4 is a cross-sectional view (not to scale) through the device of FIG. 3 and shows laminate 5 as having an inner electrically insulating film 21, nominally 3 mil thick, and an outer layer 23 of copper, nominally 1 mil thick. The dimension of film 21 provides effective gap 25. Strand 19 is wrapped as shown in FIG. 3 contacting strip 5, crossing one of the punched holes 7 of laminate strip 5, contacting the surface 3 of rod 1 and bridging the effective gaps 25 at the edges of hole 7. As can be seen, this geometry produces a triangular wicking area under strand 19 with the other two sides formed by surface 3 and effective gap 23.

Dew formation which forms and grow along the length of the strand will tend to coalesce as the individual dew droplets in the immediate vicinity of the strand touch and consequently form larger drops in the junction of the strand and the test surface.

The capillary action characteristics of the dew droplets forming along this junction will tend to fill the long slender opening immediately under the strand. This action may also tend to cause the dew to migrate toward the effective gap thereby enhancing the reliability of detection of the dew formation and causing its detection at an earlier stage of the dew accumulation. The wicking strands are almost parallel since the base of the triangle is relatively small compared to the length of the opposite side.

An open mesh screen, such as common non-metallic window screen, laid over the test surface so that it lays over the effective gap is also effective as a gathering mechanism. Many materials are useful so long as they do not conduct electricity across the effective gap either directly or by absorbing moisture or other conductive materials which would cause the same effect. The gathering mechanism needs to be substantially open to air flow to allow enough air to have relatively free access to the test surface. Generally the gathering mechanism should not close off more than about half of the test surface to the circulating air. If more test surface is closed, it can have an effect on the time constants of the emulating sink's heat absorption/adsorption. These design considerations relate to the intended applications for the device of the invention and may be readily determined as needed on a case by case basis.

Figure 5:
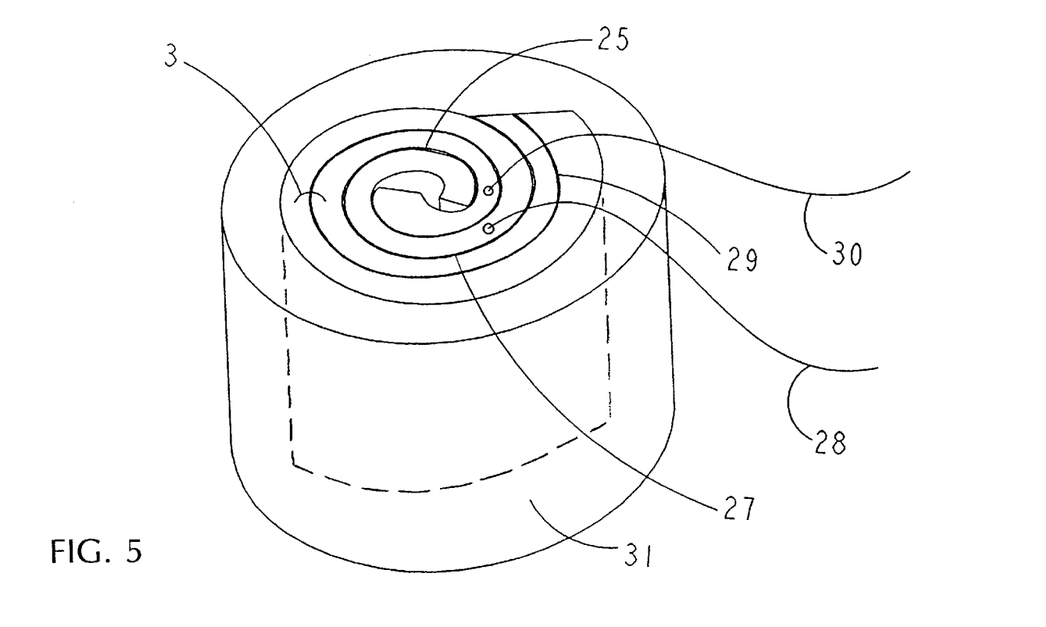
FIG. 5 depicts an alternative test surface according to the invention.

Another embodiment of a test surface according to the invention is shown in FIG. 5. This device has two copper/polyester laminate strips 27 and 29 which were laid against one another and rolled as shown. Both laminate strips can be of the identical material, or can be different. Both have copper layer 23 and insulating layer 21 which provides electrical separation between them. Strip 27 is electrically joined to one electrode of detection circuit 17 and strip 29 is connected to the other electrode. The spiral is wrapped in thermal insulating jacket 31, which covers all but the top edge of the rolled pair of copper/polyester laminates, and functions like the insulating material 2 of FIG. 1. If the polyester insulation is 0.002" thick, that provides an effective gap 25 of that dimension whose linear length is that of the resulting spiral. When the copper layer 23 is relatively thick, such as between about 0.030" and about 0.060", and has a width of the laminate strips (or depth as measured into the cylinder formed by insulating jacket 31) of as little as ⅛" to ¼", the device is thermally focused and has a surface heat density sufficient to satisfy the conditions of the invention.

Figure 6:
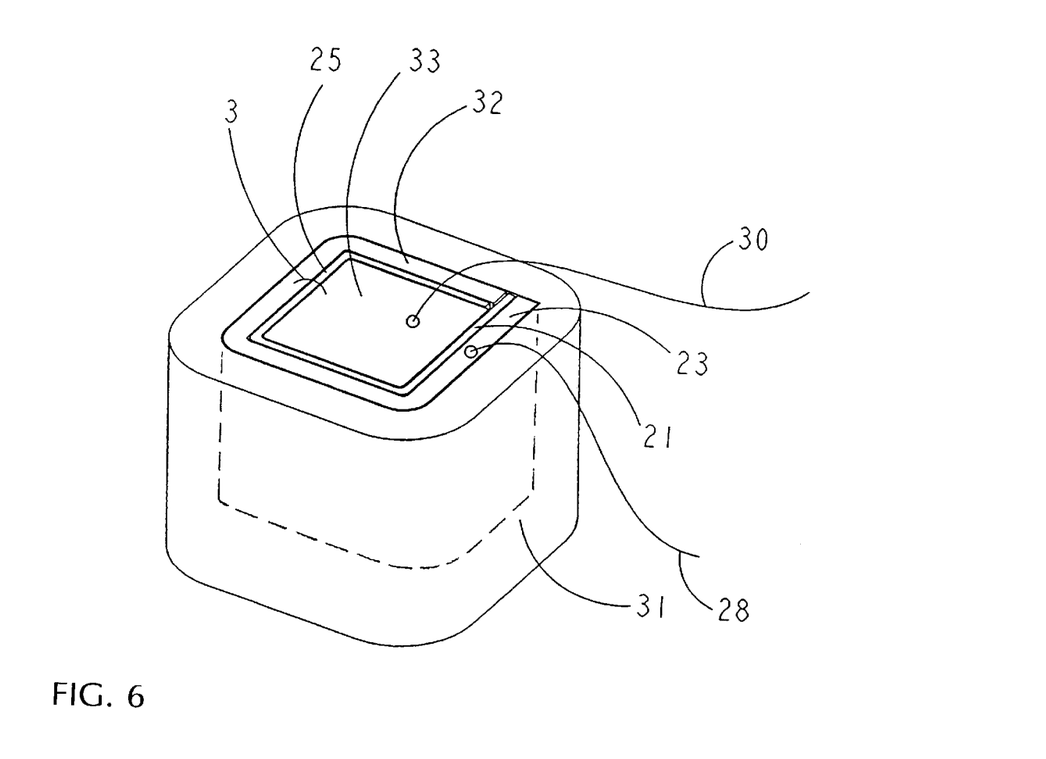
FIG. 6 shows yet another test surface according to the invention.

A third embodiment is shown in FIG. 6. A copper/polyester laminate 32 similar to the laminate strips in the previous embodiments is wrapped around a copper core of a desired shape, for example a square core 33. The thin polyester layer 21 (nom. 0.002") establishes the effective gap between the laiinate's thick copper layer 23 and the copper core 33. Core 33 is connected to the detection circuitry as one electrode, and copper layer 23 is connected as the other electrode. Thermal insulating jacket 31 surrounds all but the top surface of the wrapped core. This arrangement provides the necessary surface heat density for test surface 3, with relatively thick copper layers, such as about 0.062" thick.

Figure 7:
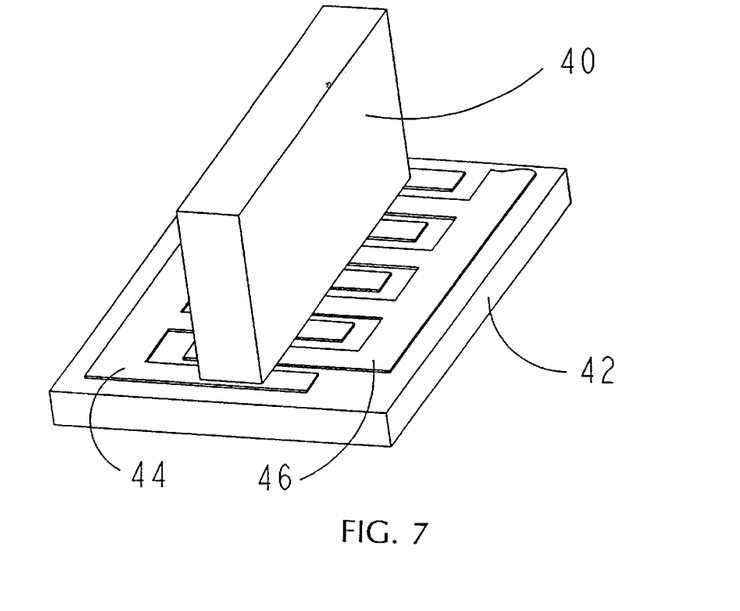
FIG. 7 shows yet another test surface according to the invention.

A fourth embodiment is shown in FIG. 7. An electrically conductive heat sink element 40 is secured to the surface of printed circuit base material 42 using non-metallic screws through the printed circuit base material into threaded holes in the bottom edge of heat sink 40. Insulating material is applied on all but the test surface which is adjacent to the base 42. Mica or other non-conducting thin (0.003–0.007") washers are placed as spacers between the bottom surface of heat sink 40 and interlaced printed circuit sensing electrode elements 44 and 46 on the surface of circuit board 42. The washers establish the effective gap, not the spacing between the printed circuit electrodes. The test surface is the surface area of the sink adjacent to the printed circuit electrodes.

The sink is not one of the electrodes, but as water condenses on its test surface, presumably, at least one drop will form on the sink's test surface and touch one of the printed circuit electrodes, and at least one other drop will form on the sink's surface that will touch the other electrode thus closing the circuit from one electrode through the first dew drop to the electrically conductive (but passive) sink, thence through the sink and to the other electrode via that second dew drop. Two dew drops are thus required—one on each of the two electrode "combs," to bridge the effective gap. For all practical purposes, two drops will rise high enough and in much the same time (i.e., in parallel) so the response time will not be significantly different than an embodiment relying on formation of a single drop at the effective gap. The conductive path is somewhat circuitous, but this is still an effective embodiment.

Figure 8:
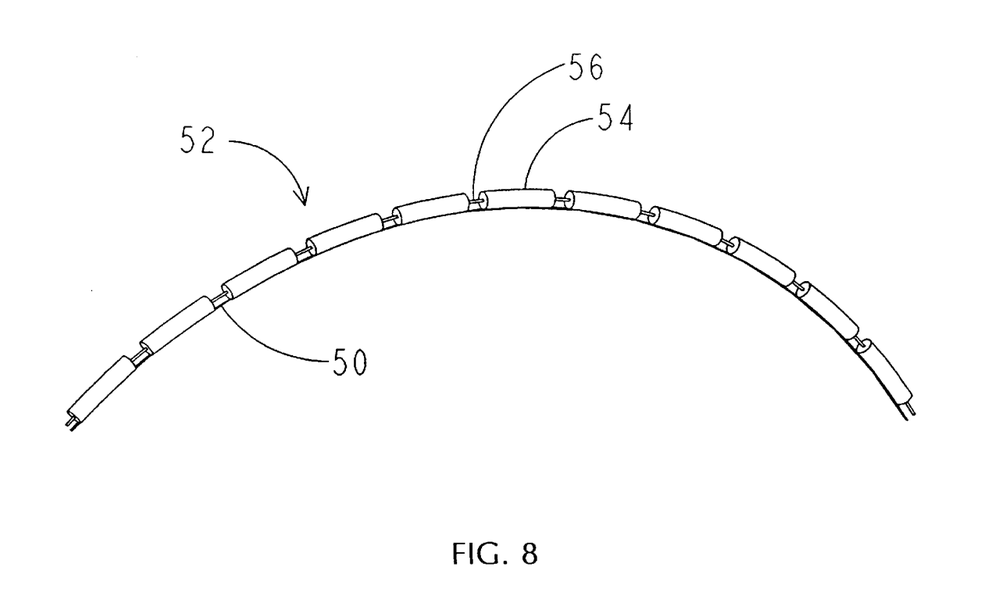
FIG. 8 depicts an alternative test surface according to the invention.

A fifth embodiment is shown in FIG. 8. Here, the test surface 50 is the surface of a metal rod that serves as the inner electrode. Magnet wire 52, comprising enamel coated portions 54 and coating-free exposed portions 56, is wound repeatedly around the rod as the outer electrode. Exposed portions 56 are about 2–3 mils wide and are formed about every one eighth inch. The effective gap is the thickness of the magnet wire's enamel coating, which may be anywhere between about 0.0005" and about 0.010".

Alternatively, a copper rod may be coated with electrically insulating material, e.g. enameled, then scratched longitudinally to the metal. Uninsulated wire is wrapped circumferentially around the grooved rod to provide an effective gap between the wire and the rod, the width of the gap being that of the enamel. The rod may be nom. 0.187" diameter, coated with 0.001" to 0.003" thick enamel. The scratches may be nom. 0.002" to 0.006" wide. The depth of the cut is not critical but may be about twice the width of the cut. The ends of the rod are thermally insulated.

Figure 9:
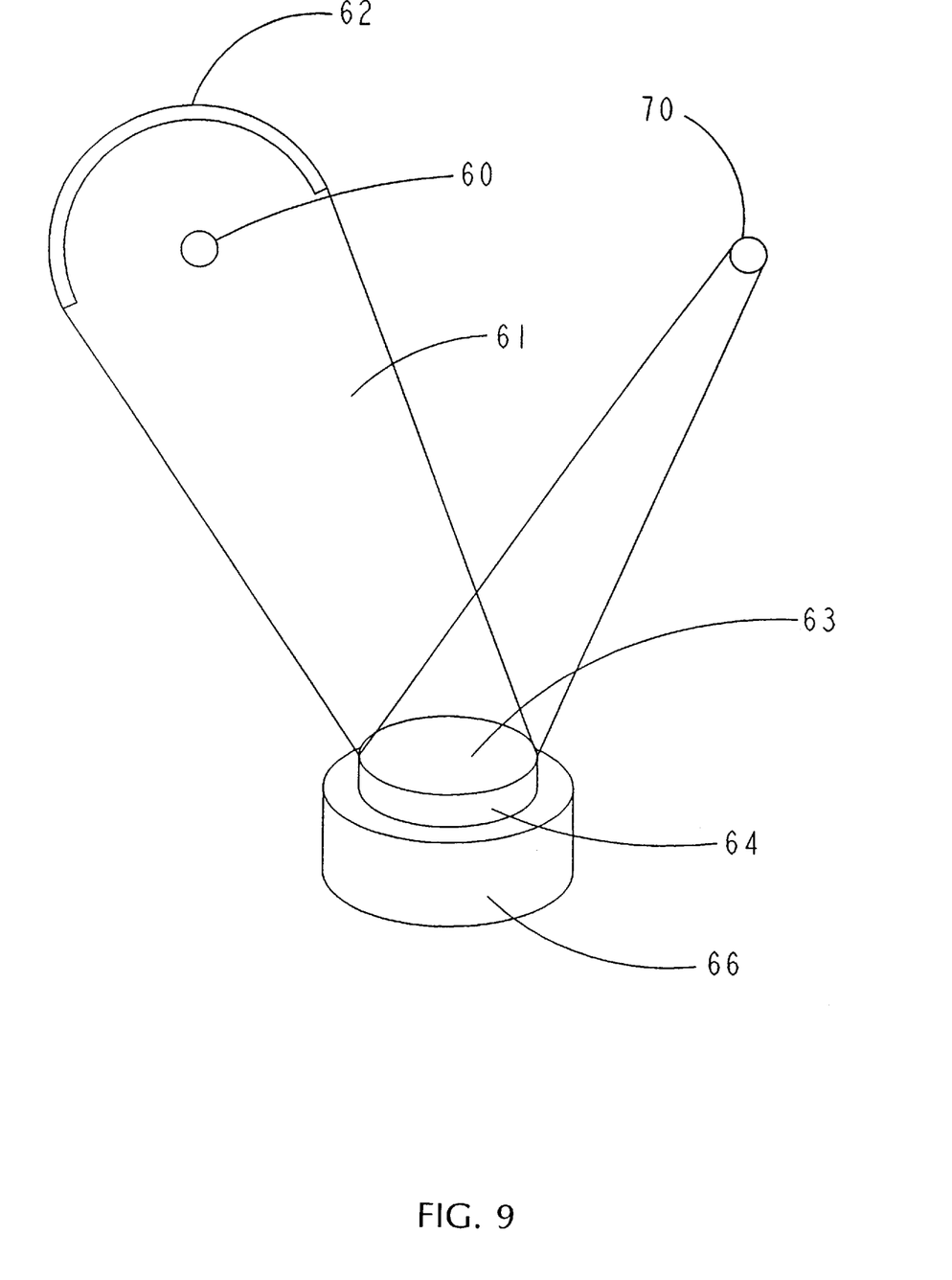
FIG. 9 shows a test surface for optical sensing according to the invention.
Figure 10:
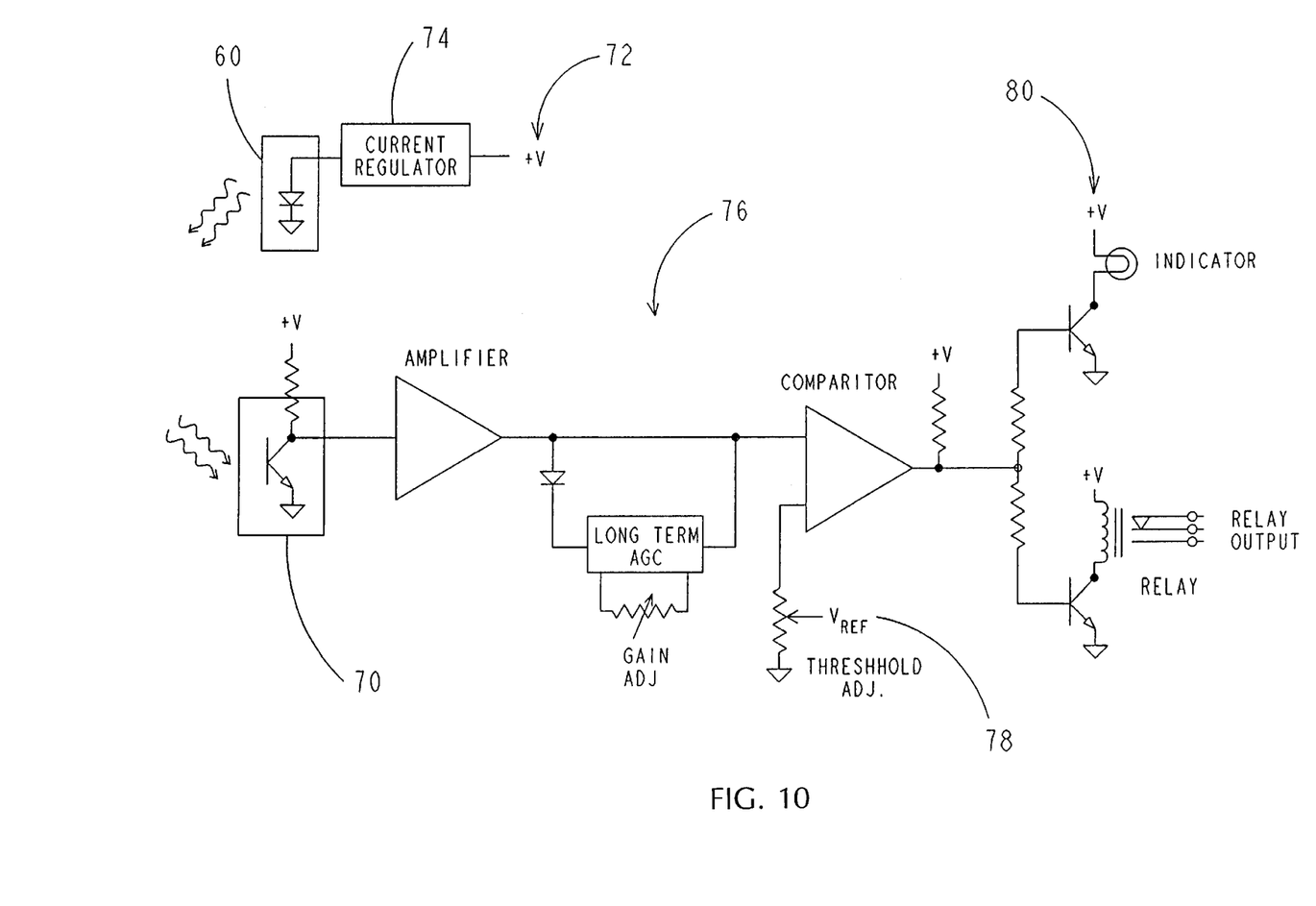
FIG. 10 shows a circuit for the optical sensing embodiment of FIG. 9.

An optical sensor embodiment is shown in FIGS. 9 and 10. Using an emulating test surface having the thermal properties described in the foregoing, the formation of dew on its exposed surface may be sensed using the change in the reflective properties of that surface of the sink as dew begins to form upon it. Its response will be a bit earlier in the dew formation process which may or may not be an advantage. It is more costly in its components and assembly than the other embodiments described, but would be preferred for a non-conductive condensate.

Light source 60 produces beam of light 61—preferably one which is narrow and well focused by reflector 62, aimed at a selected area of an exposed test surface 63 of heat sink 64 can be made to reflect that light in reflected beam 68 to a photo-sensitive detector 70 in a controlled fashion. Test surface 63 is part of heat sink 64 which has insulation 66 over a portion fit. Detector 70 is coupled to a detection circuit shown in more detail in FIG. 10, and generally comprising amplifier 76, threshold regulator 78, and output 80.

The light beam 61 and reflected beam 68 should be controlled in intensity to vary as little as practical. The selected surface is preferably polished to maximize the quantity of light it will reflect, and that polished surface will be of a material which will be unaffected by oxidation or corrosion which might cause a variation in the amount of reflected light. Slow, or long term variations in the light intensity reflected from test surface 63 may be automatically compensated for by circuits commonly referred to as "automatic gain control" (AGC) circuits incorporated in amplifier 76. Incorporating long time constants in such automatic gain circuits allows them to provide for long term changes as might be caused by slow changes in the reflectivity of that surface from oxidation or even a limited amount of surface dust, etc. Since the change in reflectivity anticipated from the formation of dew upon this surface will happen over a time which is orders of magnitude shorter than that which would be anticipated from oxidation, corrosion, dust, etc., the circuits associated with the photo-sensitive detector have no difficulty distinguishing one effect from the other. In the same way, long term variations in the intensity of light emitted from the light source due to aging and similar effects can be similarly compensated for. Short term variations caused by changes in voltage may be avoided by incorporating power regulator circuits 74 in the power source 72 applied to the light source.

The exposed test surface 63 which is used to reflect the light emitted from the light source to the photo-sensitive detector may be shaped or contoured as desired to, among other things, improve the efficiency of reflection 68 to the photo-sensitive detector. The reflective surface 63 may have a concave shape to better focus the reflected light to the photo-sensitive detector, or, it may use the parabolic shape to diminish the criticality of physical placement of the light source/photo-sensitive detector.

A first variation of the circuit associated with the photo-sensitive detector may incorporates a stable amplifying circuit 66 and an adjustable threshold detecting circuit 68 having excellent stability and a high resolution adjustments capability. In use, once the light source 60 and photo-sensitive detector 70 have been put in place relative to the reflective exposed test surface 63 of the sink, regulated power is applied to the light source and the photo-sensitive detector's circuitry. Using the high resolution adjustment of the threshold detector circuit, its sensitivity is adjusted to a point minimally above the threshold for activating this circuit's output, generally configured to cause the dew condition output 80 (an indicator, and/or output relay, etc.) to be de-energized, indicating "no dew is present".

In a second variation, the threshold regulator 78 is fixed and the gain of the power amplifier 76 is adjusted to cause the fixed threshold to be exceeded to indicate "no dew is present." Again, high resolution of the adjustments and excellent stability are required in this method. A circuit that is adjustable both at the AGC and the threshold regulator could be operated in either variation.

When conditions are such as to precipitate dew formation on the reflective test surface area of the sink as described in the foregoing, even the earliest phases of the formation of that dew will cause dramatic changes in the reflective properties of that surface. The optical properties of the forming dew are such as to diffuse the light reflected from this surface which in turn, substantially diminishes the amount of light reaching the photo-sensitive detector 70. This in turn causes the electrical energy at the threshold detection circuitry 78 to diminish to a level now below the previously established threshold. This in turn causes the activation of the "dew is present" output 80, optionally including optical indicator and/or an output relay.

As the dew ultimately evaporates from the selected surface of the sink, the electrical energy to the threshold detection circuitry will increase from the increase in light sensed at the photo-sensitive detector, and the selected threshold will again be exceeded returning the indications and outputs to the "no dew present" state.

In general, the light emitting diode or other light source 60 and photo detector 70 are biased to work in the analog region of their operational parameters. Gain and/or threshold adjustments are optional and may be fixed values. As with the circuitry used to detect dew bridging an effective gap, this circuitry has many variations and implementations which any electronic technician or engineer could design and make work with acceptable results.

An advantage of using optical sensing as compared to the sensing of current flow through dew formations bridging an effective gap as described previously, is its greater sensitivity to dew formations at a much earlier stage of that dew formation. Almost as soon as the first molecules of condensed vapor form on the selected surface of the sink, the reflective properties of that surface begins to change, decreasing the amount of light reaching the photo-sensitive sensor.

However, there are applications where this extreme sensitivity to the dew formation is not as desirable as indicating the presence of dew at a somewhat later stage of its development. Also, the manufacture of the optical sensing embodiment requires somewhat greater care and more expensive components than may be used in the embodiment which passes current through dew formations bridging the effective gap. There are no threshold or gain adjustments and there is substantially less concern for variations in the associated circuits and components in the latter embodiment.

In any of these embodiments, the configuration may be varied to provide for two types of applications. In a general area sensing configuration, all of the heat sink except the exposed test surface is insulatingly covered for example by an insulating poly-styrene plastic. Thus, the device is thermally insulated from the device on which it is mounted. While the general area sensing configuration may be appropriate in some cases, for example in an HVAC duct, there are cases where the thermal conditions on the outside of that duct wall have a greater influence on the duct wall's temperature than the air on the inside of the duct.

An alternative is a configuration that is more specifically sensitive to a specific surface—the metal wall of an HVAC duct for example. In this surface sensing configuration, the sensor better reflects the influence of the outside air on that duct wall than it would if it were sitting inside the duct in the area sensing configuration. The insulation over the very bottom end of the copper rod is removed to expose the flat bottom surface of the rod. Using a female thread in that bottom end, a small mounting hole (nom. 0.150" Diam) can be drilled through the duct wall to drive a screw into the threaded hole in the bottom of the copper rod, so as to mount the device to that duct wall. The sensor rod's end is placed in metal to metal contact with that duct wall and consequently the rod's temperature is more representative of the duct wall than of the air inside that duct, although both the rod and the duct wall are largely influenced by the temperature of the air in the duct. In the surface sensing configuration, the sensor still sits inside the duct to sense what happens when the cooled air comes down the duct, but it more precisely represents what is happening on the walls of that duct wall.

In the specific surface sensing configuration, the sensor is more likely to sense condensation which occurs less frequently during the heating season. In this situation, the workings of the dew formation reverse in a sense. If the duct wall passes through an uninsulated cold area, it becomes a cold surface. Warm, humidified air comes through the duct work to warm the area and that cold duct wall is likely to condense some of that water vapor out of the humidified air. Probably, if the heating cycle lasts long enough, the cold duct wall will be warmed enough to subsequently evaporate that condensation—but, maybe not. Depending on the factors present, pools of condensation may form which may not have an opportunity to be evaporated during the warm air cycle. For a situation like this where there are thermal influences on the surface of interest other than its normal ambient air, the configuration which is specifically sensitive to that surface will perform better.

In operation, the sensor of the invention emulates surfaces such as insulated wire, circuit boards, electrodes, cables, soldered joints, unpainted aluminum, unpainted steel, latex painted metal, plastic, glass, or any other surface of interest. The device indicates whether or not condensation is present. The quantity of condensate is not measured in a given device, but is taken into account in selecting a device for a particular application. Metal parts of surfaces of interest are generally those of greatest concern and those on which condensation forms first in greatest quantity. A broad purpose sensor therefore emulates metal surfaces and by extension is also emulating plastic, wood, and other surfaces on which large-scale condensation forms later. For condensation other than water vapor, non-metal surfaces may be of greater concern.

This discussion is intended to illustrate the broad applicability of the sensors and methods of the invention. When the sensor of the invention indicates the presence of dew, every passive article sharing its environment has at least a minimal amount of condensation on its surface. The device of the invention emulates what happens on the wide range of surfaces from styrofoam to gold, at the point when the conditions for producing dew first occurred. It does not "duplicate" their dew forming properties in that it does not need to provide quantitative information. The quantity of condensation which varies from surface type to surface type, influenced also by the material under those surfaces, but the user of products and devices does not need to know the quantity of dew in most circumstances.

If an application calls for indicating dew formation at a specific level on a specific surface—say on a precious wood artifact—one could provide a sensor according to the invention that duplicates the particular thermal characteristics of the specific surface. However, in most cases the sensor does not need to so specifically emulate, or duplicate, the surface of interest, thus saving a great deal of calculation and design for specific surfaces of interest. Also, if the application requires very early warning that an initial deposit appeared on a material of interest, an ultrasensitive sensor may be appropriate as described above, to achieve very fast response in the earliest stage of dew formation, but this may involve trade-offs with reliability.

In a ready to use embodiment, the dimensions may be nom. 0.75" diam.×. nom. 0.88" high from the mounting surface when used in an area air sensing configuration. If the end cap is removed for a surface sensing configuration, the height is reduced to nom. 0.75" high. For mounting, a clearance hole (nom. 0.15" D) may be drilled through the material (0.03" to 0.25" thick) to which the sensor is to be mounted. For example, the sensor may be mounted using a non-metallic #6-32 stud running through the drilled hole and secured with a non-metallic nut. In certain configurations, double-sided foam adhesive tape is acceptable. Other brackets, etc. may be helpful.

The operating temperature of the ready to use embodiment is about 5° to about 95° C. Humidity is not an important factor. This embodiment is generally intended for use in normal air, but is resistant to many other gases and vapors.

Related circuitry may be configured in several ways. This may be understood by referring to FIG. 2. The sensor sensing element may be provided with a 12 inch cable terminated with a miniature (0.125 inch diameter) mono phone plug. It may have a separate companion circuit module into which the cable is plugged when the sensor is to be separated from the circuit module. Or the sensor may be integrated within a circuit module as a single self-contained package. The circuit module accepts output from the sensor and provides visual and contact outputs, or an aural signal. The circuit may be as small as 3"×4"×1.5" high or less. It may run on 9V DC, with nom. 70 microamperes at idle; 40 ma with indicator & output relay activated. Thus, it may run off a standard 9V alkaline battery (nom. 0.5 ampere hour) or a 9V battery eliminator, with a 115VAC plug in supply with 9V battery button connectors, or 9V DC may be provided via an RJ11 receptacle or otherwise.

The outputs may be configured with an indicator such as a red LED that is normally off, with a user selectable real time or latched indication. Output contacts may be relay contacts accessible via an RJ11 receptacle. They may be normally open or normally closed, as selected by the user via a built-in jumper on the circuit board. They may be real time or latched as selected by the user. The outputs may allow for easy testing and reset.

In stand-alone operated or connector configuration, the circuit module may be powered via its own internal 9V alkaline battery and operated by its own on-board LED indicator and TEST button. As a connector operated module, the circuit module may be operated via an RJ11 receptacle, through which the user may apply operating power, apply a TEST input, and access the circuit's output relay contacts (selectable N/O or N/C). When those contacts are set to latch via an internal jumper, there is typically no RESET via the receptacle other than by a "power-down" of the module. RESET without powering-down the module would typically only be via a built-in push button on the circuit module.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. For example, different materials, configurations, dimensions, and circuits may be appropriate to detect condensation other than water vapor. It is therefore to be understood that, within the scope of the claims and their equivalents, the invention may be practiced otherwise than as specifically described.

What is claimed is:

1. A device for detecting condensation at a level of concern on a surface of interest in an ambient environment, comprising:
   a thermally passive detector assembly comprising a test surface that emulates the condensation-forming characteristics of the surface of interest, and a heat sink, the test surface and heat sink together having a combination of thermal conductivity, thermal capacity, and surface heat density all sufficiently high that when the test surface is located in the ambient environment, a detectable quantity of condensation forms on the test surface no later than condensation forms at the level of concern on the surface of interest; and
   a sensor that provides a signal in response to the formation of the detectable quantity of condensation on the test surface.

2. A device according to claim 1 wherein the heat sink is integral with the test surface and is not thermally insulated.

3. The device of claim 1, wherein the test surface and heat sink, in combination, have a thermal conductivity and capacity no less than that of the surface of interest.

4. The device of claim 3, wherein the heat sink is at least partially thermally insulated to increase the surface heat density of the test surface.

5. The device of claim 1, wherein the sensor comprises two electrodes, separated by an effective gap at the test surface, the presence of a droplet of condensation at the gap closing a circuit between the two electrodes.

6. The device of claim 5, wherein the effective gap is between about 0.0005 and about 0.015 inches.

7. The device of claim 5, wherein the effective gap is between about 0.002 and about 0.005 inches.

8. The device of claim 5, wherein the sensor further comprises a detection circuit comprising means for applying a voltage across the electrodes and producing a current when a condensate drop bridges the effective gap.

9. The device of claim 5, wherein one electrode is connected to the test surface and the other electrode is a wire wrapped around the test surface with first and second alternating sections, the first sections having insulation and the second sections being exposed, the thickness of the insulation of the first sections providing an effective gap between the exposed wire of the second sections and the test surface.

10. The device of claim 5, further comprising a rolled coil of two laminate pieces, each piece comprising an electrically non-conductive layer and an electrically conductive layer, the test surface being an end of the coil, and the circumference of the coil being thermally insulated, with one electrode connected to the conductive layer of one laminate piece, and the other electrode connected to the conductive layer of the other laminate piece.

11. The device of claim 5, further comprising means for gathering condensate droplets at the effective gap.

12. The device of claim 5, wherein the gathering means comprises open windings, screens, or irregular mesh, of non-water absorbing, non-wetting filamentous materials.

13. The device of claim 12, wherein the filamentous material is selected from the group consisting of fiberglass, nylon, other plastic, and a material coated with a material selected from the same group, or with wax, enamel or varnish.

14. The device of claim 1 wherein the heat sink comprises a thermally insulated extension of the test surface.

15. The device of claim 1 wherein a laminate, comprising an electrically non-conductive inner layer and an electrically conductive outer layer, is placed on the test surface, the test surface and the conductive layer being two electrodes, such that a gap is formed between the test surface and the edge of the conductive layer of the laminate, the presence of a droplet of condensation at the gap closing a circuit between the two electrodes.

16. The device of claim 15, wherein the laminate non-conductive layer is between about 0.002 and about 0.005 inches.

17. The device of claim 1, wherein the signal is a change in a switch from off to on, a visible alarm, an audible alarm, or activation of an electrical output.

18. The device of claim 1, wherein the test surface is formed of a metal rod with a diameter between about 0.125 and about 2 inches, and length from about half to about three times the diameter.

19. The device of claim 1, wherein the sensor comprises a basal surface having first and second exposed electrodes, and the test surface is adjacent to and spaced apart from the electrodes by a gap, such that the simultaneous presence of a first droplet of condensation between the test surface and the first electrode and of a second droplet of condensation between the test surface and the second electrode closes a circuit between the two electrodes and the test surface.

20. The device of claim 1, further comprising a light source directed at the test surface, wherein the sensor comprises a photo-sensitive detector.

21. The device of claim 20, wherein the sensor further comprises a detection circuit comprising an automatic gain control circuit, an amplifying circuit, and a threshold detecting circuit.

22. The device of claim 1, wherein the test surface is thermally connected with the surface of interest by physical contact.

23. The device of claim 1, wherein the test surface is thermally insulated from the surface of interest.

24. The device of claim 1, wherein the test surface and surface of interest are in the same ambient environment, and the test surface is physically isolated from the surface of interest.

25. A system comprising a plurality of devices according to claim 1, and a condensation control system comprising means for eliminating condensation activatable in response to a signal from one or more of the devices.

26. A device according to claim 1, further comprising a condensation control system comprising means for eliminating condensation activatable in response to a signal from the sensor.

27. A device according to claim 26, wherein the means for eliminating condensation comprises a heater or dehumidifier.

28. A device for detecting condensation at a level of concern on a surface of interest, comprising:
   (a) means for emulating the condensation-forming characteristics of the surface of interest,
   (b) means for passively thermally focussing the emulating means comprising a heat sink having a combination of thermal conductivity, thermal capacity, and surface heat density all sufficiently high that a detectable quantity of condensation forms on the emulating means no later than formation of condensation at the level of concern on the surface of interest; and
   (c) means for detecting the presence of the detectable quantity of condensation on the emulating means.

29. A condensation sensor comprising a test surface, a laminate applied thereto, and a detection circuit, the test surface being electrically connected to the detection circuit as a first electrode, the laminate comprising an electrically non-conductive inner layer having a thickness of about 0.001" to about 0.010" placed on the test surface, and the laminate further comprising an electrically conductive outer layer electrically connected to the detection circuit as a second electrode, such that the thickness at the edge of the inner layer of the laminate forms a gap between the test surface and the outer layer of the laminate, the presence of a droplet of condensation at the gap closing a circuit between the two electrodes, and permitting detection in the detection circuit.

30. A method for detecting condensation at a level of concern on a surface of interest in an ambient environment, comprising:
   (a) providing a test surface in the ambient environment,
   (b) emulating the condensation-forming characteristics of the surface of interest with the test surface,
   (c) passively thermally focussing the test surface by means of a heat sink, the test surface and the heat sink together having a combination thermal conductivity, thermal capacity, and surface heat density sufficiently high that a detectable quantity of condensation forms on the test surface no later than formation of condensation at the level of concern on the surface of interest; and
   (d) detecting the presence of the detectable quantity of condensation on the test surface as a signal in a detection circuit.

31. The method of claim 30, further comprising the step of activating a means for eliminating the detectable quantity of condensation in response to the signal.

* * * * *